US012582318B2

(12) United States Patent
Anders et al.

(10) Patent No.: US 12,582,318 B2
(45) Date of Patent: Mar. 24, 2026

(54) ILLUMINATION UNIT AND MEDICAL IMAGING SYSTEM FOR FLUORESCENCE IMAGING IN OPEN SURGERY

(71) Applicant: OLYMPUS Winter & Ibe GmbH, Hamburg (DE)

(72) Inventors: Konrad Anders, Hamburg (DE); Matthias Dissel, Hamburg (DE); Carsten Holthaus, Barsbuettel (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 178 days.

(21) Appl. No.: 18/382,271

(22) Filed: Oct. 20, 2023

(65) Prior Publication Data

US 2024/0268673 A1     Aug. 15, 2024

Related U.S. Application Data

(60) Provisional application No. 63/444,620, filed on Feb. 10, 2023.

(51) Int. Cl.
*A61B 5/00*          (2006.01)
*A61B 34/20*         (2016.01)
(Continued)

(52) U.S. Cl.
CPC ............ *A61B 5/0071* (2013.01); *A61B 90/30* (2016.02); *A61B 90/361* (2016.02);
(Continued)

(58) Field of Classification Search
CPC ....... A61B 90/30; A61B 90/361; A61B 90/36; A61B 2090/304; A61B 2090/306; A61B 2090/308; A61B 2090/309; A61B 2090/3614; A61B 2090/373; A61B 5/0071; A61B 34/20; A61B 2034/2055;
(Continued)

(56) References Cited

U.S. PATENT DOCUMENTS 5,980,454 A * 11/1999 Broome ................... A61B 1/05
                                                        359/615
6,615,071 B1 * 9/2003 Casscells, III ....... A61B 5/6853
                                                        600/549

(Continued)

FOREIGN PATENT DOCUMENTS

DE        102021132814 A1      6/2023

*Primary Examiner* — Marcela I. Shirsat
(74) *Attorney, Agent, or Firm* — Scully, Scott, Murphy & Presser, P.C.

(57)          ABSTRACT

An illumination unit for illuminating an area of operation during open surgery. The illumination unit including: a body; a fiber bundle configured to guide light towards a distal end of the body, and a reflector body arranged at the distal end of the body. Where at least a part of the fiber bundle is guided inside the body along a longitudinal direction, the fiber bundle is split up into a plurality of optical fibers which form a fiber layer on an inner surface of the body, end faces of the plurality of optical fibers are arranged at the distal end of the body, the reflector body encloses the end faces of the plurality of optical fibers in a radial direction and extends distally beyond the distal end of the body in the longitudinal direction, and an inner surface of the reflector body is a reflective surface.

14 Claims, 3 Drawing Sheets

(51) Int. Cl.

| | |
|---|---|
| *A61B 90/00* | (2016.01) |
| *A61B 90/30* | (2016.01) |
| *F21V 7/00* | (2006.01) |
| *F21V 7/04* | (2006.01) |
| *F21V 7/06* | (2006.01) |
| *F21V 8/00* | (2006.01) |
| *F21Y 115/10* | (2016.01) |
| *G02B 6/04* | (2006.01) |

(52) U.S. Cl.
CPC ............. *G02B 6/0008* (2013.01); *G02B 6/04* (2013.01); *A61B 34/20* (2016.02); *A61B 2034/2055* (2016.02); *A61B 2034/2065* (2016.02); *A61B 2090/306* (2016.02); *A61B 2090/308* (2016.02); *A61B 2090/309* (2016.02); *A61B 2090/3614* (2016.02); *A61B 2090/373* (2016.02); *F21V 7/0008* (2013.01); *F21V 7/0058* (2013.01); *F21V 7/04* (2013.01); *F21V 7/06* (2013.01); *F21V 2200/10* (2015.01); *F21V 2200/13* (2015.01); *F21V 2200/17* (2015.01); *F21Y 2115/10* (2016.08)

(58) Field of Classification Search
CPC ............. A61B 2034/2065; F21V 13/02; F21V 7/0008; F21V 7/0033; F21V 7/0058; F21V 7/04; F21V 7/06; F21V 2200/10; F21V 2200/13; F21V 2200/17; F21W 2131/205; F21Y 2113/20; F21Y 2115/10; G02B 6/0008; G02B 6/04
USPC .......................................... 362/572; 600/248
See application file for complete search history.

(56) References Cited

U.S. PATENT DOCUMENTS 6,697,666 B1 *  2/2004  Richards-Kortum ....................... A61B 5/0071 600/478
2014/0107496 A1  4/2014  Hellstrom et al.
2014/0357948 A1  12/2014  Kikuchi et al.

* cited by examiner

ILLUMINATION UNIT AND MEDICAL IMAGING SYSTEM FOR FLUORESCENCE IMAGING IN OPEN SURGERY

CROSS-REFERENCE TO RELATED APPLICATION

The present application is based upon and claims the benefit of priority from U.S. Provisional Application No. 63/444,620 filed on Feb. 10, 2023, the entire contents of which is incorporated herein by reference.

BACKGROUND

Field

The present disclosure relates to an illumination unit configured to illuminate an area of operation during open surgery. The present disclosure further relates to a medical imaging system for fluorescence imaging in open surgery.

Prior Art

In open surgery, video capturing units are often placed in the operating room to record the operating area. Such video capturing units usually comprise a camera head augmented by an optical imaging unit and an illumination unit.

A camera head usually comprises one or more optical sensors as well as a cone adapter connecting and securing the ocular cones of optical imaging units to the camera head. Such optical imaging units may be devices for endoscopic procedures, such as rigid telescope type endoscopes having an optical assembly at their distal tip for forming an image of the specified field of view, and one or more relay lens units for relaying the image to the endoscope's ocular for view with the unaided eye, or alternatively, the camera head. For this purpose, the camera head comprises imaging optics that focus on the location of the virtual image projected by the ocular lens of the attached telescopes at their own focal distance. This focal distance is standardized between different types of telescopes, since they have to be usable with the unaided eye.

For the purpose of capturing the operating area, the optical imaging units are often designed to image the operating area with a predefined field of view at a predefined working distance. A typical example is the so-called exo-scope, which resembles a short endoscope with an objective lens, a set of relay lens units and an eyepiece. The optical properties of the objective lens are quite different from those of objective lenses of endoscopes because of their very different focal lengths, since, unlike an endoscope, an exo-scope is designed to operate outside a human body instead of inside the human body.

Since the camera head has its own imaging optics, an attachment lens system, also called a head lens, may be attached to the camera head's cone adapter that provides the combined optical system of the attachment lens system and the camera head's optical imaging system with the focal length and other optical properties necessary for viewing and recording the operating area.

In order to illuminate the operating area, the medical imaging systems usually comprise an illumination light generating unit comprising one or more light sources generating the illumination light. The illumination light is transported from the illumination light generating unit to the distal end of an optical imaging unit through a fiber bundle, where it exits the fiber bundle. Endoscopes and exoscopes usually do not comprise any light shaping units at the tip, so that the irradiance distribution at the field of operation is mainly defined by the irradiance distribution with which the light enters the fiber bundle from the light source.

Modern medical imaging systems implement the above-described versatility of endoscopic or open surgery imaging with various telescopes and exoscopes for different applications that can be attached to the system's camera head, which is controlled by a central control unit (CCU). The telescopes and exoscopes may have an illumination light connector to be connected to an illumination light generating unit of the medical imaging system via light fibers. Such systems may furthermore implement fluorescence imaging for fluorescence imaging guided surgery.

Fluorescence imaging is a form of molecular imaging, which generally encompasses imaging methods for visualizing and/or tracking of molecules having specific properties that are used for molecular imaging. Such molecules can be substances that are endogenous to the body, or dyes or contrast agents that are injected into the patient. MRI and CT, for example, therefore, also fall under the term "molecular imaging". Fluorescence imaging as a variant of molecular imaging uses the property of certain molecules (fluorophores), which emit light of certain wavelengths when excited/absorbed by light of certain wavelengths.

For the purpose of fluorescence imaging, the system's camera head includes sensors that are sensitive in the visible spectrum and in the near infrared spectrum, while the system's illumination light generating unit has a light source for white light to illuminate the operating area with white light as well as at least one excitation light source designed to illuminate the operating area with light that includes an excitation wavelength capable of exciting a fluorescent substance or dye that has been injected into the operating area, to return fluorescence emission. The excitation light source may comprise a laser or a light emitting diode, the wavelength depending on the dye used. For indocyanine green (ICG), e.g., which emits fluorescence light between 750 nm and 950 nm, an excitation wavelength may be between 600 nm and 800 nm. After being excited, the dyes shed the excitation energy by emitting light at slightly longer wavelengths than the excitation light. Other wavelengths may be used as excitation wavelengths depending on the type of dye used. This can include wavelengths that are further inside the visible spectrum.

In fluorescence imaging, it is important that a sufficient light intensity of the excitation light is provided at the field of operation in order to gain a sufficient intensity of the fluorescence light. However, the irradiance distribution of the excitation light is often larger than the field of operation. This results in a low light intensity in the region where the light is actually required. In order to narrow the light beam, a lens unit may be employed to focus the emitted light. However, such a lens unit is difficult to manufacture, has high manufacturing costs and creates problems when disinfecting the optical components in an autoclave.

SUMMARY

An object is to provide an illumination unit and a medical imaging system for fluorescence imaging in open surgery, which illuminate an area of operation with a high light intensity.

Such object can be solved by an illumination unit configured to illuminate an area of operation during open surgery, wherein the illumination unit comprises a body and a fiber bundle configured to guide light towards a distal end of the body, at least a part of the fiber bundle is guided inside the body along a longitudinal direction, the fiber bundle is split up into a plurality of optical fibers which form a fiber layer on an inner surface of the body, end faces of the optical fibers are arranged at the distal end of the body, the illumination unit comprises a reflector body arranged at the distal end of the body, the reflector body enclosing the end faces of the optical fibers in a radial direction and extending beyond the distal end of the body in the longitudinal direction, and an inner surface of the reflector body is a reflective surface.

The illumination unit can be configured to illuminate the field of view of an optical imaging unit during open surgery. The illumination light can be generated by an illumination light generating unit and guided to the illumination unit. In the illumination unit, the light can be guided in the plurality of optical fibers of the fiber bundle. Inside the body, the fiber bundle can be split up into the individual optical fibers to form the fiber layer on the inner surface of the body. The optical fibers can extend along the longitudinal direction on the inner surface of the body to the distal end of the body. There, light rays are emitted from the end faces of the optical fibers. The reflective surface of the reflector body can be arranged and configured to reflect an outer part of the emitted light rays towards a central axis of the illumination unit. In reflecting this outer part of the light rays back inwards, the irradiance distribution gets narrower so that it may match the field of view of the optical imaging unit. In addition, the irradiance in the center increases. Thus, the total light intensity in the field of view can be increased.

According to an embodiment, the illumination unit can comprise a light source. Alternatively, the illumination unit can be configured to receive light from a light source, which can be arranged inside the illumination light generating unit. The illumination unit can be configured as an illumination adapter device, which can be configured to be connected to a camera head.

For a part of its length, the fiber bundle can take the shape of a compact bundle. This compact bundle can be split up in the body into the individual optical fibers to cover the inner surface of the body. The fiber layer can be guided in at least one guiding slot of the body. The guiding slot can extend in the longitudinal direction to align the optical fibers with the longitudinal direction before the light is emitted. This can provide a homogeneous illumination.

The body, the reflector body and/or the entire illumination unit can be a solid of revolution, wherein an axis of revolution can be the central axis of the exoscope. The body can be a tubular body.

An end face of the body can be flush with the end faces of the optical fibers. Thus, the light can be emitted from the end faces of the optical fibers exactly at the end face of the body.

The central axis can extend through the middle of the body in the longitudinal direction. The longitudinal direction is a length direction of the illumination unit and the body. The radial direction is orthogonal to the central axis and to the longitudinal direction. Inside the body, light can be guided along the longitudinal direction for at least a part of the length of the body. A direction of light propagation can be the direction in which the light is guided inside the illumination unit.

The optical fibers can be arranged in an annular shape in the body. By distributing the optical fibers in an annular shape, the fiber bundle can be arranged symmetrically inside the body. The individual optical fibers of the fiber layer can run along the longitudinal direction, while the fiber layer can be curved in a plane orthogonal to the longitudinal direction. The fiber layer can have an annular shape in the plane orthogonal to the longitudinal direction.

The end faces of the optical fibers can form a ring shaped exit face. A ring shaped exit face can provide a homogenies radiance distribution at the distal end.

The body can comprise a cylindrical opening, wherein the opening can be configured to receive at least one component of the optical imaging unit. Thus, the component of the optical imaging unit can be arranged concentrically in the illumination unit. The opening can be configured to receive a lens unit of the optical imaging unit. In this way, the exoscope can record images of the area of operation with the optical imaging unit and at the same time illuminate the area of operation with the illumination unit arranged around the optical imaging unit.

The illumination unit can be part of an exoscope tip or a fluorescence imaging adapter connected with or capable of being connected with a camera head. The fluorescence imaging adapter can comprise the illumination unit and a component of the optical imaging unit. The fluorescence imaging unit can comprise an ocular cone configured to mechanically connect the fluorescence imaging adapter to the camera head. In this way, the fluorescence imaging unit does not require its own image sensors.

The body of the illumination unit can comprise an outer hull element, a fiber guiding element and a tubular element. The tubular element can be configured to receive the component of the optical imaging unit. The fiber guiding element can be arranged around the tubular element in the radial direction and comprise one or more guiding slots in which the fiber layer can be arranged. The outer hull element can be arranged outside the fiber guiding element and the tubular element in the radial direction.

The reflective surface of the reflector body can have a convex, concave or parabolic shape. With a reflector shaped formed in any of these shapes, the light rays emitted from the end faces of the optical fibers can be guided efficiently towards the central axis of the body. The reflective surface can be configured to reflect the outer part of the emitted light in a way that an angle between rays of the outer part of the emitted light and the central axis can be decreased due to the reflection.

The reflector body can be cone shaped. A cone shaped reflector can reflect the outer light rays back towards the central axis. A diameter of the reflector body can increase in the direction of light propagation. A gradient along the reflector surface of the reflector body can increase or decrease in the direction of light propagation.

According to an embodiment, the reflective surface of the reflector body can be made of aluminum or can comprise aluminum. The entire reflector body can be made of aluminum. Aluminum reflects light without significant losses in intensity and can be easily disinfected in an autoclave.

The reflective surface can comprise a protective coating. The protective coating can prevent damage to the reflective surface that may occur during storage or during an operation.

The illumination unit can comprise an ocular cone forming a rear part of a hull of the illumination unit, wherein the ocular cone can be configured to be connected to an adapter of a camera head. The ocular cone can be configured to act as an eye piece funnel for the illumination unit and can be configured to form an adapter between the illumination unit and a camera head or an exoscope tube of an exoscope.

Such object can be further solved by a medical imaging system for fluorescence imaging in open surgery comprising an optical imaging unit and an illumination unit according to one of the previously described embodiments arranged concentrically around the optical imaging unit.

The same or similar advantages apply to the medical imaging system as previously mentioned with respect to the illumination unit. The medical imaging system can also comprise a camera head or an exoscope body configured to be connected to the illumination unit. The fiber bundle can extend through the exoscope body of the exoscope to the exoscope tip. According to a different embodiment, the fiber bundle can be connected to the light source arranged outside the illumination unit. In this embodiment, the fiber bundle can extend from the light source, which can be arranged in the illumination light generating unit, to the body of the illumination unit and can enter the body through an opening in the body. The opening can be arranged with an oblique angle to the central axis of the body.

BRIEF DESCRIPTION OF THE DRAWINGS

Further characteristics will become apparent from the description of the embodiments together with the claims and the included drawings. Embodiments can fulfill individual characteristics or a combination of several characteristics.

The embodiments are described below, without restricting the general intent of the invention, based on exemplary embodiments, wherein reference is made expressly to the drawings with regard to the disclosure of all details that are not explained in greater detail in the text. In the drawings.

In the drawings, the same or similar types of elements or respectively corresponding parts are provided with the same reference numbers in order to prevent the item from needing to be reintroduced.

DETAILED DESCRIPTION

Figure 1:
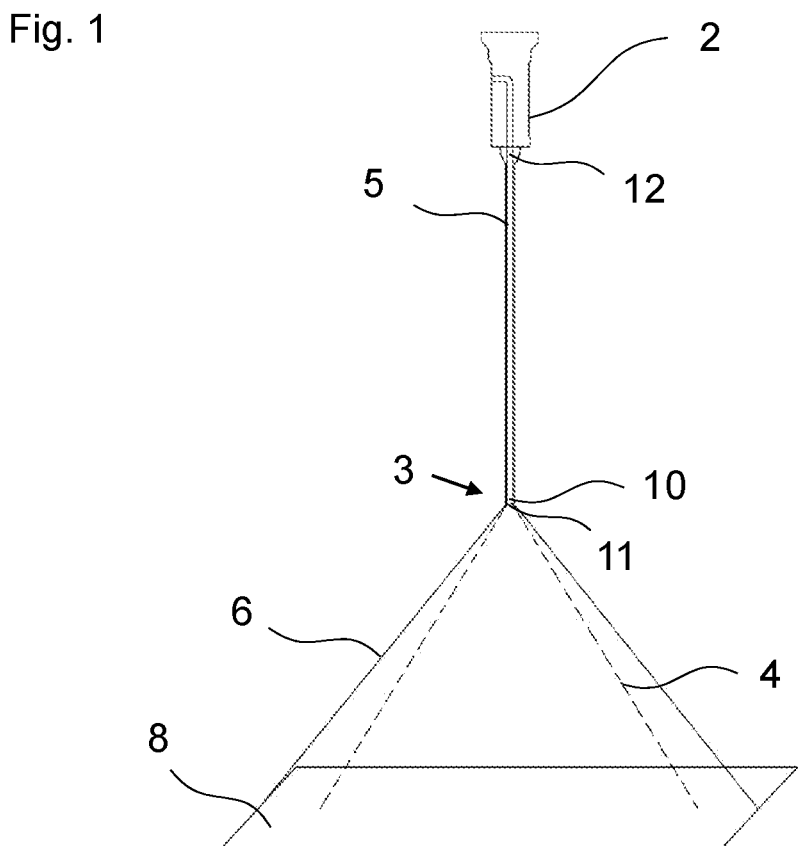
FIG. 1 illustrates a schematic simplified representation of an exoscope arranged to illuminate and record an area of operation.

FIG. 1 shows a schematic simplified representation of a medical imaging device, namely an exoscope 2 configured to observe and illuminate an area of operation 8. The exoscope 2 comprises an optical imaging unit 5 and an illumination unit arranged inside the exoscope 2. The optical imaging unit 5 records an image of the area of operation 8 within a field of view 4, which is indicated with dashed lines. The illumination unit comprises a fiber bundle 12 to guide light from a light source, which is not shown in FIG. 1, to an exoscope tip 10 at a distal end 3 of the exoscope 2 in order to illuminate an illuminated area 6. When the light is emitted at a distal end 11 of the exoscope tip 10 from the fiber bundle 12, the illuminated area 6 is usually larger than the field of view 4. Thus, the light intensity is comparatively low inside the field of view 4, as a lot of the emitted light intensity is wasted in areas outside the field of view 4.

Figure 2:
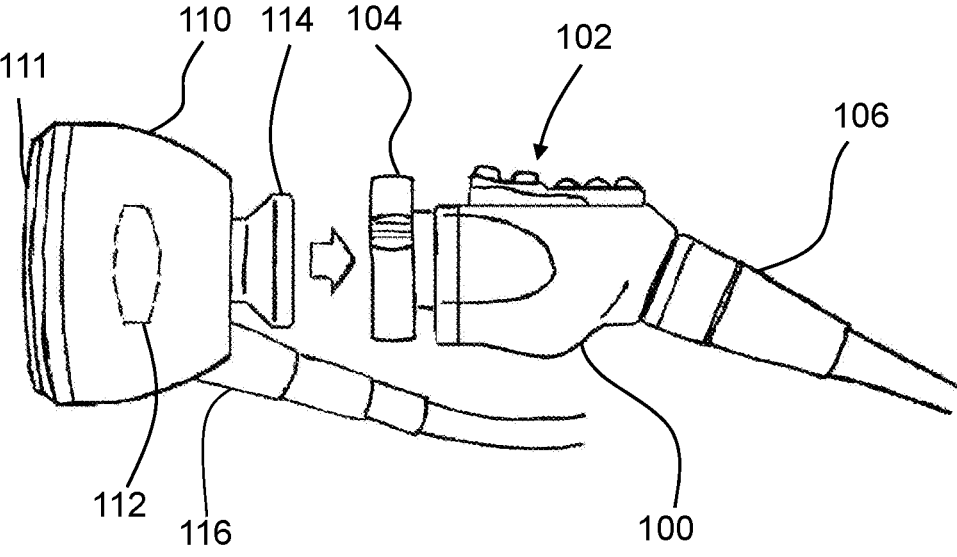
FIG. 2 illustrates a schematic simplified representation of a camera head with a fluorescence imaging adapter.

FIG. 2 illustrates a schematic representation of another medical imaging device, namely a combination of a camera head 100 and a fluorescence imaging adapter 110. The camera head 100 is configured for white light imaging as well as fluorescence imaging. It is handheld and has control buttons 102 on the top of its housing, an adapter 104 for attachment of various optics systems at its front surface and a connecting cable 106 for power and signal transmission leading to a central control unit (not shown). Since the camera head 100 is configured to receive telescope type endoscopes with eyepieces (ocular cones), its adapter 104 may be configured to receive such eyepieces. The imaging optics of the camera head 100 is configured to have its focus at a location where the typically attached endoscopes project a virtual image to be viewed with the naked eye through the eyepiece. The eyepieces of endoscopes are usually adjusted so that the virtual image is about one meter in front of the eyepiece (−1 diopter). The exit pupil of the endoscopes is configured to approximately match the entrance pupil of the camera head and is located about 7 mm behind the edge of the eyepiece funnel, which is typically inside adapter 104 in the attached state.

The fluorescence imaging adapter 110 differs from endoscopes and exoscopes in that it does not have imaging optics, i.e., it does not produce a virtual image. Instead, it provides a head lens or attachment lens in the form of a head lens system 112 having one or more individual lenses whose function it is to change the properties of the imaging optics of camera head 100, rendering the camera head 100 capable of viewing the operating field. This can be done, e.g., by decreasing the focal length of the camera head 100 and thereby enlarging its field of view. Although the head lens system 112 itself does not provide a virtual image to be viewed with the naked eye, the fluorescence imaging adapter has a standardized ocular cone 114 on its rear side for the purpose of connecting to the adapter 104 of camera head 100.

Furthermore, the fluorescence imaging adapter 110 is equipped with a light guide cable 116 leading towards its front surface 111. The other end of the light guide cable 116 may be connected to an illumination light generating unit (not shown).

Figure 3:
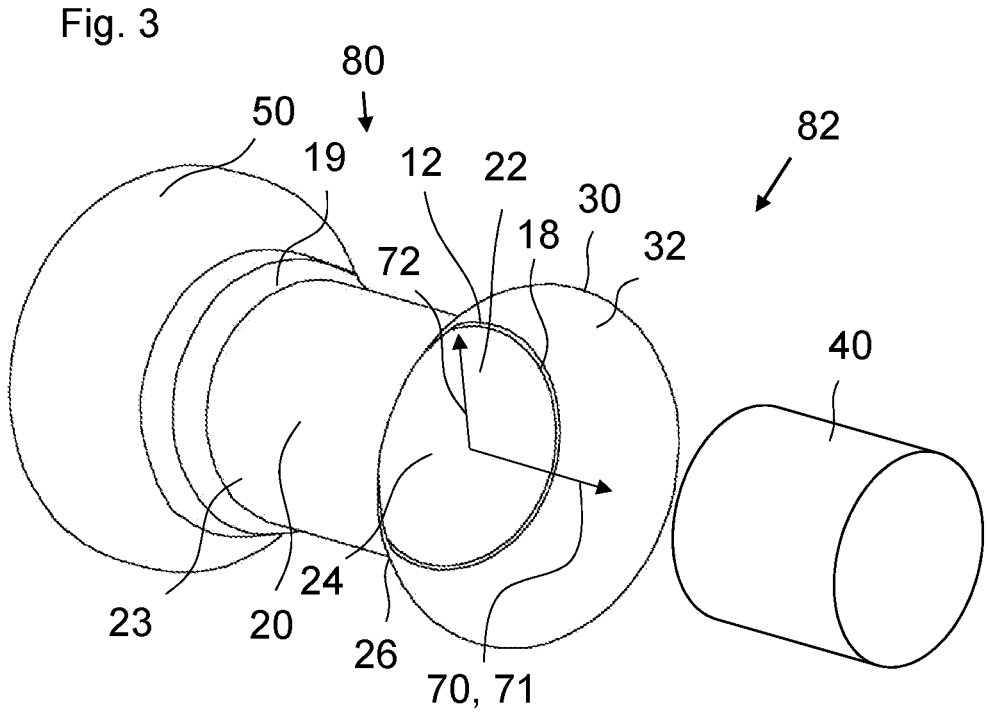
FIG. 3 illustrates a schematic simplified perspective representation of an illumination unit with a reflector body.

FIG. 3 shows a perspective drawing of an illumination unit 80 configured to increase the light intensity inside the field of view 4. The illumination unit 80 comprises an ocular cone 50, a body 20 in the shape of a tube and a reflector body 30. The illumination unit 80 is part of a medical imaging system 82, which may also comprise a component 40 of the optical imaging unit 5, for example a lens unit. The illumination unit 80 may be arranged at the exoscope tip 10 of an exoscope as shown in FIG. 1 or may form a part of fluorescence imaging unit 110 as shown in FIG. 2.

In the body 20, the fiber bundle 12 is split up and arranged on an inner surface 22 of the body 20 in an annular shape. At a distal end 26 of the body 20, the fiber bundle 12 forms an exit face 18 in the form of a ring. The reflector body 30 comprises a reflective surface 32 surrounding the exit face 18 of the fiber bundle 12 in a radial direction 72. When light is emitted from the exit face 18, the outer part of the emitted rays is reflected by the reflective surface 32 back towards a central axis 71.

The body 20 also comprises a central opening 24 configured to receive the component 40 of the optical imaging unit 5. In FIG. 3, the component 40 is arranged outside of the opening 24. However, during assembly of the exoscope 2, the component 40 will be put inside the opening 24. In this arrangement, the exit face 18 of the illumination unit is arranged around the component 40 of the optical imaging unit 5, so that the area of operation 8 can be recorded and illuminated at the same time and with a symmetrical illumination.

The fiber bundle 12 may extend along a longitudinal direction 70 on the inner surface 22 of the body 20. In the embodiment shown in FIG. 3, the outer surface 23 of the body 20 forms a hull 19 of the illumination unit 80 together with the ocular cone 50 and the reflector body 30.

Figure 4:
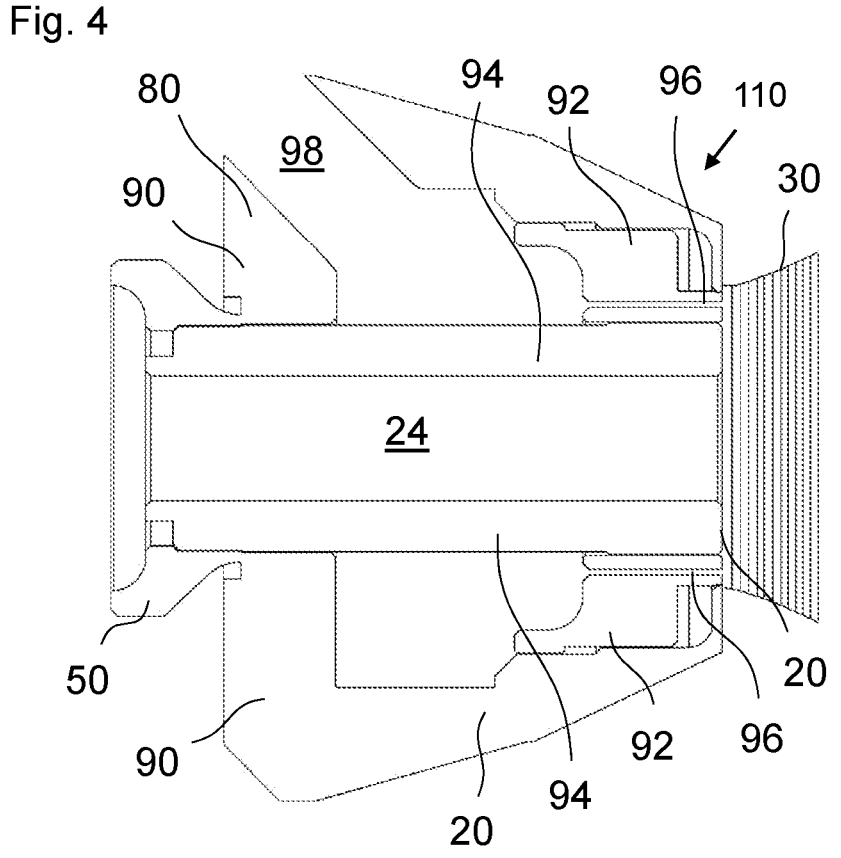
FIG. 4 illustrates a schematic simplified cross sectional representation of a fluorescence imaging adapter with a reflector body.

FIG. 4 shows another exemplary embodiment of an illumination unit 80 with a reflector body 30. A reflective surface 32 of the reflector body 30 has a convex shape. In this embodiment, the illumination unit 80 is part of a fluorescence imaging adapter 110. The body 20 of the illumination unit 80 comprises an outer hull element 90, a fiber guiding element 92 and a tubular element 94. The outer hull element 90 forms the outer hull of the body 20 and comprises an opening 98, which is configured to receive the fiber bundle 12. For sake of clarity, the fiber bundle 12 is not shown in FIG. 4. The fiber guiding element 92 is arranged concentrically inside the outer hull element 90 and comprises one or more guiding slots 96, which are configured to guide the optical fibers of the fiber layer once the fiber bundle 12 has been split up. The guiding slots 96 guide the optical fibers in the longitudinal direction such that the optical fibers are not bent at the distal end 26 of the body 20. The fiber guiding element 92 concentrically surrounds the tubular element 94, which comprises the opening 24 to receive the component 40. The optical fibers of the split up fiber bundle 12 are arranged surrounding the outer surface of the tubular element 96.

Figure 5:
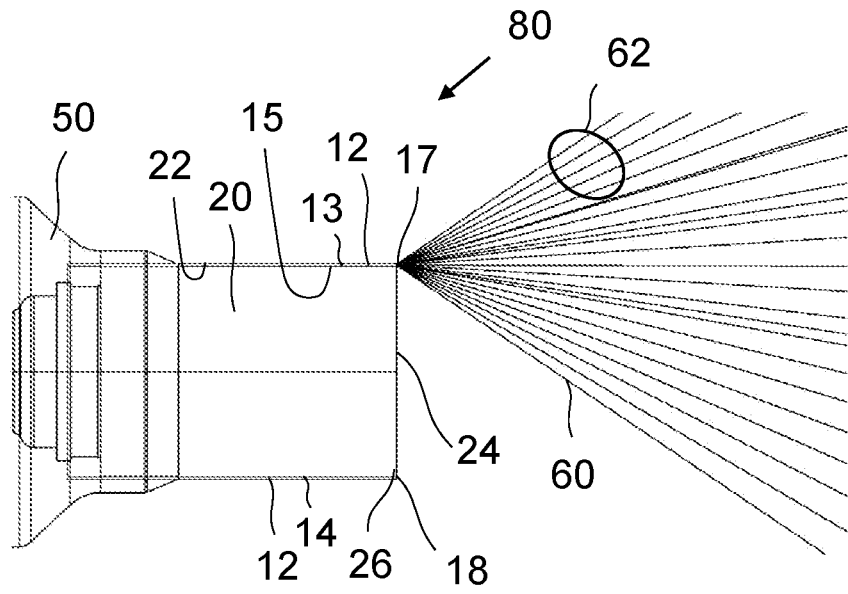
FIG. 5 illustrates a schematic simplified cross sectional representation of an illumination unit without a reflector body.
Figure 6:
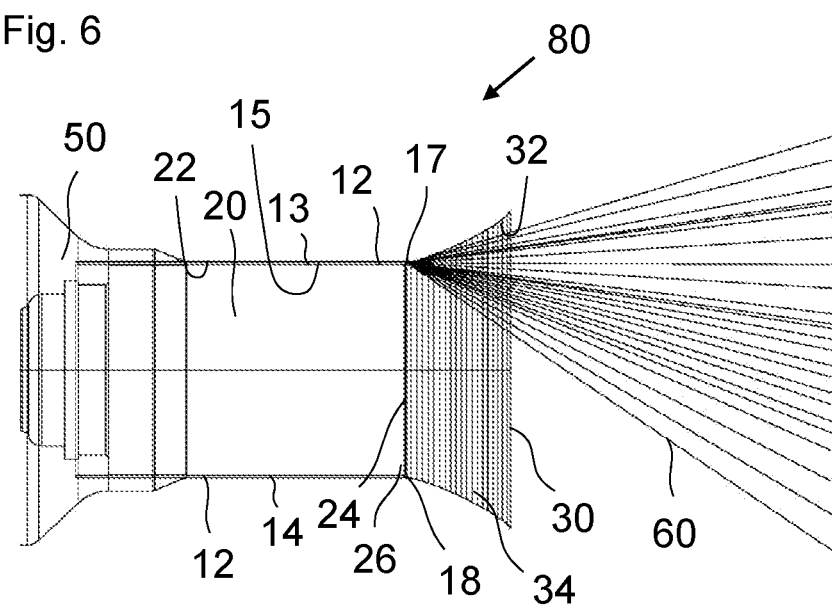
FIG. 6 illustrates a schematic simplified cross sectional representation of an illumination unit with a reflector body, showing the change in the light path of the emitted light rays.

In FIGS. 5 and 6, the effect of the reflector body 30 on the size and shape of the illuminated area 7 is demonstrated. FIGS. 5 and 6 both show cross sectional representations of different embodiments of an illumination unit 80. In FIG. 6, the illumination unit 80 comprises a reflector body 30 with a convex reflective surface 32, while in FIG. 5 there is no reflector body 30. As can be seen in the cross sectional views of FIGS. 4 and 5, the optical fibers 13, 14 of the fiber bundle 12 form a fiber layer 15 on the inner surface 22 of the body 20. At the end faces 17, 18 of the optical fibers 13, 14, light rays 60 are emitted. However, for the sake of clarity, only the light rays 60 emitted from the upper optical fiber 13 are shown in FIGS. 5 and 6. When comparing the light rays 60 in FIG. 5 with the light rays 60 in FIG. 6, it is evident that an outer part 62 of the light rays 60 in FIG. 6 is reflected back towards the central axis 71 by the reflective surface 32 of the reflector body 30 in FIG. 6. Thus, the reflector body 30 achieves a narrower illuminated area 6 and thus increases the light intensity inside the field of view 4. Due to the reflector body 30, the irradiance distribution is narrower and there is less light in the area outside the field of view 4. In addition, the maximum irradiance in the center of the illuminated area 6 is higher in the embodiment shown in FIG. 6 than in the embodiment shown in FIG. 5 without the reflector body 30.

The reflective surface 32 or the entire reflector body 30 may comprise aluminum or may be made entirely out of aluminum. In addition, the reflective surface 32 may comprise a protective coating 34, which is indicated by vertical lines in FIGS. 4 and 6. This protective coating protects the reflective surface 32 from damage to provide a good illumination quality.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCES 2 exoscope
3 distal end
4 field of view
5 optical imaging unit
6 illuminated area
8 area of operation
10 exoscope tip
11 distal end
12 fiber bundle
13, 14 optical fiber
15 fiber layer
16, 17 end face
18 exit face
19 hull
20 tubular body
22 inner surface
23 outer surface
24 opening
26 distal end
30 reflector body
32 reflective surface
34 coating
40 component
50 ocular cone
60 light rays
62 outer part
70 longitudinal direction
71 central axis
72 radial direction
80 illumination unit
82 medical imaging system
90 outer hull element
92 fiber guiding element
94 tubular element
96 guiding slot
98 opening
100 camera head
102 control buttons
104 adapter for attachment devices
106 connecting cable
110 fluorescence imaging adapter
112 head lens system
114 ocular cone
116 light guide cable

What is claimed is:

1. An illumination unit for illuminating an area of operation during open surgery, the illumination unit comprising:

a body;

a fiber bundle configured to guide light towards a distal end of the body, and a reflector body arranged at the distal end of the body;

wherein at least a part of the fiber bundle is guided inside the body along a longitudinal direction, the fiber bundle is split up into a plurality of optical fibers which form a fiber layer on an inner surface of the body, end faces of the plurality of optical fibers are arranged at the distal end of the body, the reflector body is arranged radially outside from the end faces of the plurality of optical fibers relative to a central axis of the body to reflect a radially outer portion of the light emitted from the plurality of optical fibers towards the central axis, the reflector body extending distally beyond the distal end of the body in the longitudinal direction, and an inner surface of the reflector body is a reflective surface.

2. The illumination unit according to claim 1, wherein the plurality of optical fibers are arranged in an annular shape in the body.

3. The illumination unit according to claim 1, wherein the end faces of the plurality of optical fibers form a ring shaped exit face.

4. The illumination unit according to claim 1, wherein the body comprises a cylindrical opening, wherein the cylindrical opening is configured to receive at least one component of an optical imaging unit.

5. The illumination unit according to claim 1, wherein the illumination unit is one of a part of an exoscope tip or a fluorescence imaging adapter configured to be connected with a camera head.

6. The illumination unit according to claim 1, wherein the reflective surface of the reflector body has one of a convex, a concave or a parabolic shape.

7. The illumination unit according to claim 1, wherein the reflector body is cone shaped.

8. The illumination unit according to claim 1, wherein the reflective surface of the reflector body is made of aluminum or comprises aluminum.

9. The illumination unit according to claim 1, wherein the reflective surface comprises a protective coating.

10. The illumination unit according to claim 1, further comprising an ocular cone forming a rear part of a hull of the illumination unit.

11. The illumination unit according to claim 10, wherein the ocular cone is configured to be connected to an adapter of a camera head.

12. A medical imaging system for fluorescence imaging in open surgery, the medical imaging system comprising:

an optical imaging unit; and an illumination unit according to claim 1 arranged concentrically around the optical imaging unit.

13. An exoscope comprising the illumination unit according to claim 1.

14. A fluorescence imaging adapter comprising the illumination unit according to claim 1.

* * * * *